US00PP37727P2

(12) United States Plant Patent
Simon et al.

(10) Patent No.: US PP37,727 P2
(45) Date of Patent: Oct. 6, 2026

(54) SWEET BASIL PLANT NAMED 'RUVOB10'

(50) Latin Name: *Ocimum basilicum*
Varietal Denomination: RUVOB10

(71) Applicant: Rutgers, The State University of New Jersey, New Brunswick, NJ (US)

(72) Inventors: James E. Simon, Princeton, NJ (US); Utsav Kumar, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 19/259,850

(22) Filed: Jul. 3, 2025

(51) Int. Cl.
*A01H 5/02* (2018.01)
*A01H 5/12* (2018.01)
*A01H 6/50* (2018.01)

(52) U.S. Cl.
USPC ..... Plt./258
CPC ..... *A01H 6/506* (2018.05)

(58) Field of Classification Search
USPC ..... Plt./258
CPC ..... A01H 5/02; A01H 5/12
See application file for complete search history.

*Primary Examiner* — Kent L Bell
(74) *Attorney, Agent, or Firm* — Klarquist Sparkman, LLP

(57) ABSTRACT

A new and distinct *Ocimum basilicum* plant named 'RUVOB10' distinguished by its white and green variegation leaf pattern with creamy white margins, bold, Genovese-like sweet and peppery flavor, green stems with an upright, moderately bushy habit with a slightly open V-shaped canopy, and seedling lethal phenotype.

2 Drawing Sheets

Latin name of the genus and species of the plant claimed: *Ocimum basilicum.*

Variety denomination: 'RUVOB10'.

BACKGROUND

The present application relates to a new and distinct variety of sweet basil plant named 'RUVOB10'. The new plant was discovered in an $F_3$ population derived from a cross between 'Rutgers Obsession-DMR' (U.S. Pat. No. 10,159,212) and 'Aroma 2' (unpatented) sweet basil varieties. The original cross between 'Rutgers Obsession DMR' and 'Aroma 2' was made in 2022 in New Brunswick, New Jersey. 'RUVOB10' was identified in 2023 in the 3$^{rd}$ generation (F3) from the initial cross F1. The plant was selected due to its unique leaf variegation phenotype, when growing in a cultivated area in New Brunswick, New Jersey, USA

SUMMARY

'RUVOB10' exhibits striking white and green variegated leaves, making it visually distinctive and desirable for ornamental and specialty culinary applications. However, seeds collected from the variegated basil produce seedlings having white cotyledons that appear to lack chlorophyll, leading to non-viable offspring that die within 10 days of germination. As a result, this variety is asexually reproduced, typically by vegetative cloning (cuttings/tissue culture).

'RUVOB10' can be distinguished from other sweet basil varieties at least due to the following unique combination of characteristics:

Consistent white and green variegation with creamy white margins, which range from 0.2 mm to 0.6 mm on a fully matured leaf, and midrib areas flanked by olive green.

Bold, Genovese-like sweet and peppery flavor.

Green stems with an upright, moderately bushy habit with a slightly open V-shaped canopy.

Seedling lethal phenotype.

The female parent, 'Rutgers Obsession-DMR', has uniform dark green, concave leaves (upward cupping), and has a floral flavor with a warm and slightly spicy undertone. In comparison, 'RUVOB10' exhibits stable white and green variegated, convex leaves (downward cupping), and has an intensely floral flavor with slightly peppery and fruity notes. The leaves of 'Rutgers Obsession-DMR' are also flatter relative to 'RUVOB10'.

The male parent, 'Aroma 2' has glossy, uniform dark green leaves that are narrow and elliptical (reaching up to 7 cm in length), long internodes, and a standard upright Genovese form. In contrast, 'RUVOB10' exhibits stable white and green variegated leaves that are medium ovate to medium elliptic, has an upright, moderately bushy habit with a slightly open V-shaped canopy. 'Aroma 2' and 'RUVOB10' both have a similar Genovese-type flavor profile, however, 'RUVOB10' has a slightly peppery finish. In addition, 'RUVOB 10' is resistant to downy mildew whereas 'Aroma 2' is not resistant.

In contrast to both the female and male parents, which can be seed propagated, seed from 'RUVOB10' produces non-viable seedlings, which appears to be due to a chlorophyll deficiency (white cotyledons). In addition, 'RUVOB10' presents a highly ornamental appearance that makes it attractive for dual culinary and decorative use, while 'Rutgers Obsession-DMR' and 'Aroma 2' are primarily for culinary use.

The most similar known commercial variety to 'RUVOB10' is 'Pesto Perpetuo' (U.S. Plant Pat. No. 16,260), a variegated basil cultivar that has a compact, columnar growth habit, purple stems, and small upright leaves. The leaf variegation of 'Pesto Perpetuo' typically appears as uniform white margins on lime green foliage, and it is known for having a mild, citrusy flavor that is characteristic of *Ocimum* x *citriodorum* hybrids. In contrast, 'RUVOB10' has green stems, an upright, moderately bushy habit with a slightly open V-shaped canopy, and medium ovate to medium elliptic leaves. The variegation of 'RUVOB10' appears as irregular patches of white and green throughout the leaf surface, giving it a more dynamic appearance than 'Pesto Perpetuo'. In addition, 'RUVOB10' exhibits a bold, mildly peppery, Genovese-type basil flavor and aromatic profile marked by high linalool, eugenol, and α-trans-bergamotene content (at least 50% linalool, at least 3% eugenol, and at least 2% α-trans-bergamotene, see, Table 1), making it especially attractive to culinary users who value both flavor and visual appearance. Unlike the sterile 'Pesto Perpetuo', which does not flower or set seed, 'RUVOB10' will flower and set seed; however, the seeds produce non-viable seedlings.

'RUVOB10' was first asexually propagated by vegetative cuttings in 2023 in New Brunswick, New Jersey. Subsequent asexual reproduction of this new variety by vegetative cuttings shows that the foregoing characteristics come true to form, are firmly fixed, and are established and transmitted through succeeding propagations.

Certain phenotypic characteristics of this variety may naturally change with changing environmental conditions (such as photoperiod, temperature, moisture, soil conditions, nutrient availability, or other factors). Color descriptions and other terminology are used in accordance with their ordinary dictionary descriptions, unless the context clearly indicates otherwise. Color designations (hue/value/chroma) are made with reference to The Royal Horticultural Society Colour Chart (R.H.S.), 5$^{th}$ edition, London, England, 2007.

BRIEF DESCRIPTION OF THE DRAWING(S)

Figure 1:
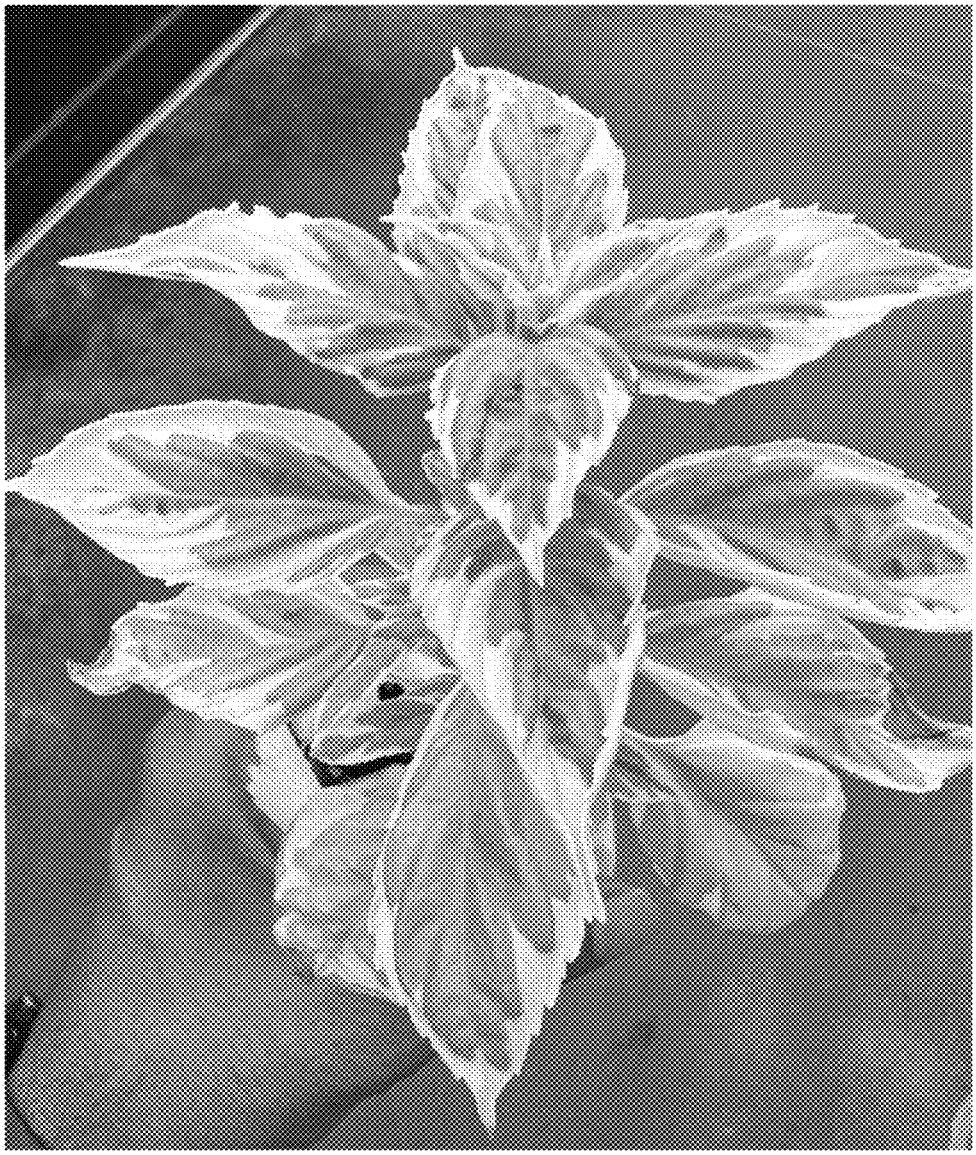
FIG. 1 is a photograph showing a 7-week old plant that was grown in a greenhouse under a HPS (High Pressure Sodium) lamp. This photo was taken under ambient light conditions in the greenhouse in July 2023.
Figure 2:
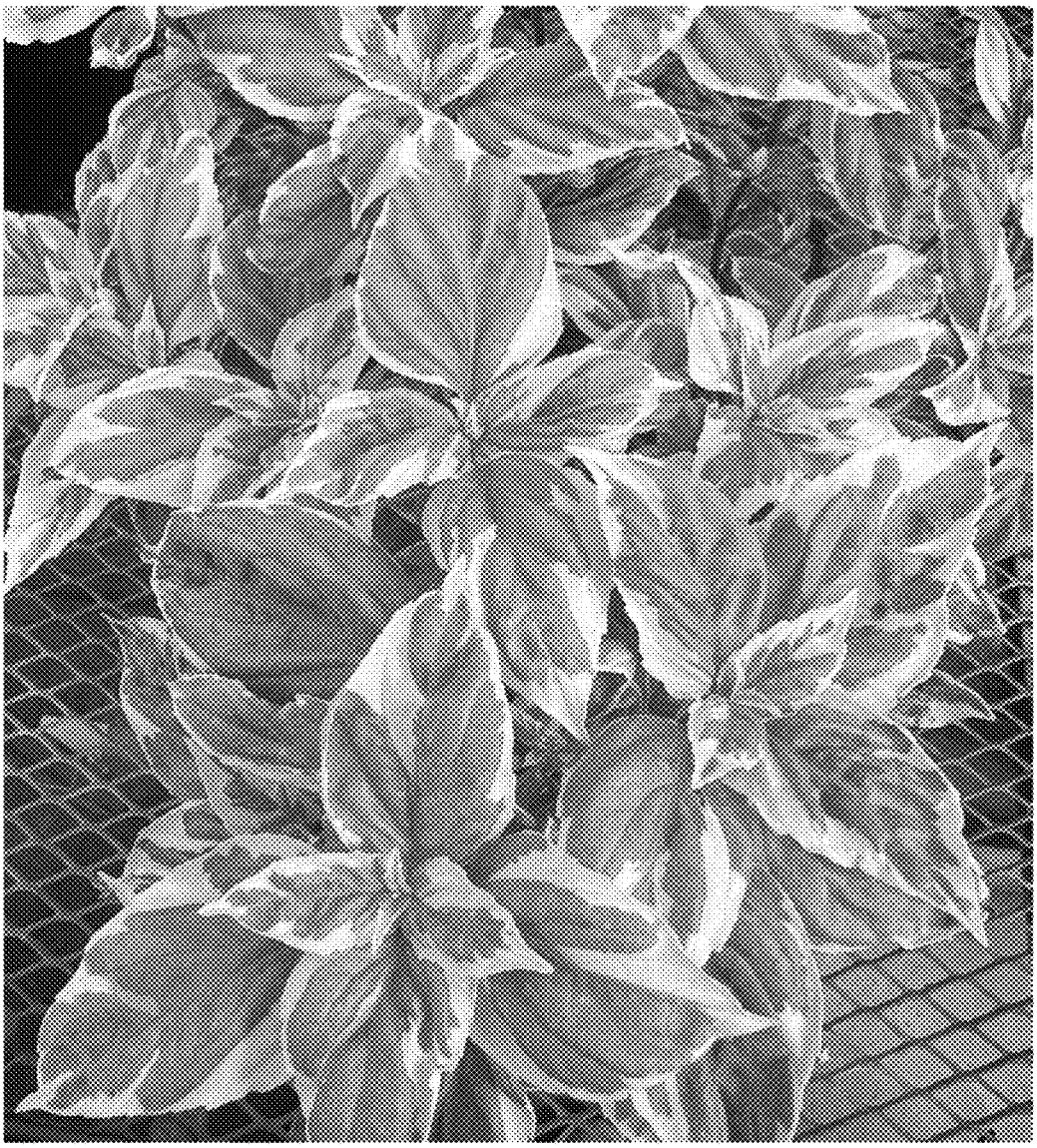
FIG. 2 is a photograph showing a 10-week old plant that was grown in a greenhouse under a HPS (High Pressure Sodium) lamp. This photo was taken under ambient light conditions in the greenhouse in March 2025.

The color photographs show typical specimens of the new variety and depict the color as nearly true as is reasonably possible to make the same in color illustrations of this character. It should be noted that colors may vary, for example due to lighting conditions at the time the photographs are taken. Therefore, color characteristics of this new variety should be determined with reference to the observations described herein, rather than from the photographs alone.

DETAILED DESCRIPTION

The following detailed description of 'RUVOB10' is based on observations of asexually reproduced progeny 10-weeks of age unless context indicates otherwise. The following detailed description concerns plants growing in pots in a controlled greenhouse in New Brunswick, NJ. The color values were determined in May 2025 under natural light conditions in New Brunswick, NJ.

Parentage:

*Female parent*.—'Rutgers Obsession-DMR'.

*Male parent*.—'Aroma 2'.

Plant:

*Growth habit*.—Upright, moderately bushy with a slightly open v-shaped canopy.

*Plant height*.—60-70 cm.

*Plant spread*.—35-40 cm.

*Vigor*.—Moderate to High.

*Hardiness*.—USDA Zones 9-11.

Leaves:

*Shape*.—Medium ovate to medium elliptic.

*Size*.—Length: 6-9 cm. Width: 3-4.5 cm.

*Color*.—Immature Leaf: The central green portion of the upper surface is closest to RHS 147C, while the creamy white margins are closest to RHS 157D. On the lower surface, central grayish green is closest to RHS 194B with pale variegated area closest to RHS 158D. Mature Leaf: The central green portion of the upper surface is closest to RHS 147C with creamy white margins closest to RHS 157D. The lower surface central green area closest to RHS 194B and margins closest to RHS 155A.

*Arrangement*.—Opposite.

*Apex shape*.—Acute.

*Base shape*.—Cuneate to rounded.

*Margin*.—Slightly serrated.

*Teeth*.—Present, but shallow.

*Leaf texture*.—Upper Surface: Smooth to slightly ruffled. Lower Surface: Smooth.

*Venation pattern*.—Pinnate.

*Color of veins*.—Upper Surface: RHS 145D. Lower Surface: RHS 148C.

*Petiole*.—Color: RHS 146D. Length: 1.7 cm. Width: 2 mm. Texture: Smooth.

Stem:

*Shape*.—Cylindrical.

*Color*.—Young stem tissue near the top is closest to RHS 144C, the mid stem region is closest to RHS 157C, and the basal stem region is slightly brown closest to RHS 199D.

*Diameter*.—3-6 mm.

*Surface texture*.—Smooth.

*Internode length*.—1.9-3.4 cm.

*Branching*.—12-13 primary branches per plant when the plant is about 13 weeks old grown under greenhouse conditions. Primary branches are approximately 23.1 cm long (range: 19.8-24.5 cm, n=5) with diameters of approximately 4-6 mm near the midpoint. Stems and branches are cylindrical and smooth. Young stem near the apex is closest to RHS 144C, maturing to RHS 157C along the mid stem and RHS 149D near the base (mostly on older primary branches).

*Leaves per branch*.—A typical primary branch bears approximately 118-324 leaves when the plant is about 13 weeks old grown under greenhouse conditions.

Roots:

*Root initiation*.—Under greenhouse propagation conditions, vegetative cuttings of 'RUVOB10' initiate visible roots in approximately 7-9 days after sticking in soil, and develop a well branched root system suitable for transplanting after approximately 14-20 days.

*Root habit*.—The root system is fine and fibrous, with multiple roots emerging from the basal node and lower stem. Roots are moderately dense, typically 1-2.5 cm long at 8 days after sticking, and are concentrated around the basal portion of the cutting before filling the upper half of the substrate.

*Color*.—Fresh roots are white NN155C.

Flowers:

*Inflorescence*.—Spike, cluster of six.

*Flowers per inflorescence*.—60+.

*Petals per flower*.—5.

*Petal arrangement*.—Five petals in a bilabiate structure.

*Petal shape and size*.—Ovate; the lower lip is formed by 3 fused petals and the upper lip by 2 single lobes. Individual petals are approximately 9 mm long, the upper 2 lobes are about 3 mm wide and the three fused lower lip lobes are about 0.8 mm wide at the tip. Petal lobes are ovate with entire margins and bases fused into the corolla tube.

*Petal texture*.—Upper and lower petal surfaces are soft and slightly hairy.

*Petal color*.—White to very pale lavender, closest to RHS 155D (both surfaces).

*Stamen number*.—4.

*Filament size*.—Approximately 7 mm long and 1.5 mm wide.

*Filament color*.—RHS 155D.

*Anther color*.—RHS NN155C.

*Pollen*.—Abundant, color is closest to RHS 11B.

*Pistil number*.—1.

*Pistil length*.—1.2 cm.

*Style length*.—1 cm.

*Style color*.—Closest to RHS 155D.

*Stigma size*.—Approximately 1.2 cm long and 1.5 mm wide.

*Stigma color*.—Closest to RHS 155D.

*Stigma shape*.—Bifurcated.

*Ovary*.—Ovoid with 4 lobes approximately 2 mm long and 1.5 mm wide, color closest to RHS 160A.

*Sepals*.—Arrangement: Five sepals fused into a tubular calyx with triangular lobes. Color: RHS 145D. Shape: Triangular lobes. Size: 5 mm long and 2 mm wide. Number: 5. Apex: Acuminate. Margins: Entire. Base: Fused. Texture: Both inner and outer sepals surfaces are pubescent.

*Bud*.—Shape: Ovoid. Length: 3 mm. Diameter: 2 mm. Color: RHS 157C.

*Pedicel size*.—Approximately 4 mm long and 1.5 mm in diameter.

*Pedicel texture*.—Smooth.

*Pedicel color*.—Closest to RHS 144C.

*Date of bloom*.—80-90 days under greenhouse production.

*Lastingness*.—Individual flowers remain open and fresh for approximately 3-5 days before senescing.

*Self-compatibility*.—Yes.

*Fragrance*.—Classic basil scent.

Seed:

*Seed size*.—1.2 mm in length and 1 mm in width.

*Seed weight*.—1.24 mg.

*Color*.—RHS 202A.

*Number of seed per capsule*.—4.

*Texture*.—Seeds are smooth with a matte seed coat surface and no visible reticulation or ridging under a hand lens.

Leaf volatiles: Plants of 'RUVOB10', 'Rutgers Obsession DMR', and 'Aroma 2' were grown side by side under the same greenhouse conditions in New Brunswick, New Jersey. Tissue was harvested at the vegetative stage, when plants were fully leafy and prior to flowering. For each genotype, 20 fully expanded leaves were collected, oven dried at 40° C. for 72 hours and then ground to obtain a homogeneous dry tissue. Volatile compounds from the dried basil were extracted using headspace solid phase microextraction (SPME) and analyzed by gas chromatography mass spectrometry (GCMS) with three replicate samples per genotype. Results are provided in Table 1, and expressed as mean relative abundance (area % ±standard deviation) of each compound in the dry leaf volatile fraction.

TABLE 1

Relative abundance of volatile aroma compounds in dried leaf tissue. Values represent the mean relative abundance (area % ± standard deviation) of each compound in the dry leaf volatile fraction from headspace SPME GCMS.

| Volatile | 'Aroma 2' | 'Rutgers Obsession DMR' | 'RUVOB10' |
|---|---|---|---|
| Linalool | 46.5 ± 3.92 | 40.42 ± 8.1 | 62.37 ± 2.4 |
| Eugenol | 2.57 ± 0.86 | 4.63 ± 1.39 | 5.11 ± 2.09 |
| α-trans-bergamotene | 0.09 ± 0.02 | 2.88 ± 0.42 | 3.69 ± 0.59 |

Headspace SPME GCMS of dried leaf tissue shows that 'RUVOB10' has a linalool dominant Genovese-type profile with elevated floral and spicy notes. In the dry samples, 'RUVOB10' contained the highest linalool (62.37%±2.4), highest eugenol (5.11%±2.09), and highest α-trans-bergamotene (3.69%±0.59) relative to its parents. Together, these data support that 'RUVOB10' combines a strong, floral linalool backbone with enhanced spicy (eugenol) and warm, fruity (α-trans-bergamotene) notes compared with either parent.

While environmental factors, sampling time, methods of analysis, and other factors can influence the quantitation of volatile compounds, high concentrations of these three volatiles (at least 50% linalool, at least 3% eugenol, and at least 2% α-trans-bergamotene), are typical of 'RUVOB10'.

Additional description:

*Use*.—Culinary or ornamental.

*Flavor*.—Classic Genovese sweet basil with slightly peppery finish.

*Aroma*.—Strong sweet basil scent which has intensely floral with slight peppery fruity notes.

*Disease/pest resistance*.—Resistant to *Peronospora belbahrii* (downy mildew).

We claim:

1. A new and distinct *Ocimum basilicum* plant named 'RUVOB10' substantially as illustrated and described herein.

* * * * *